United States Patent [19]

Carr

[11] Patent Number: 5,198,776
[45] Date of Patent: Mar. 30, 1993

[54] MICROWAVE SYSTEM FOR DETECTING GASEOUS EMBOLI

[75] Inventor: Kenneth L. Carr, Harvard, Mass.

[73] Assignee: Microwave Medical Systems, Inc., Littleton, Mass.

[21] Appl. No.: 721,107

[22] Filed: Jun. 26, 1991

[51] Int. Cl.[5] .......................... G01R 27/04; A61B 5/05; A61M 31/00
[52] U.S. Cl. .................. 324/639; 128/653.1; 128/DIG. 13; 604/50; 73/19.1
[58] Field of Search .................. 324/639; 128/653.1, 128/DIG. 13; 604/50, 65; 333/26; 73/19.1, 19.01

[56] References Cited

U.S. PATENT DOCUMENTS

| | | | |
|---|---|---|---|
| 3,956,695 | 5/1976 | Stamm | 324/639 |
| 4,135,131 | 1/1979 | Larsen et al. | 128/653.1 |
| 4,280,495 | 7/1981 | Lampert | 604/50 |
| 4,532,151 | 11/1985 | Bolomey et al. | 128/653.1 |
| 4,647,281 | 3/1987 | Carr | 604/50 |
| 4,715,727 | 12/1987 | Carr | 324/632 |
| 4,938,079 | 7/1990 | Goldberg | 604/65 |
| 5,057,782 | 10/1991 | Brown et al. | 324/639 |
| 5,073,167 | 12/1991 | Carr et al. | 604/114 |

Primary Examiner—Jack B. Harvey
Assistant Examiner—Maura K. Regan
Attorney, Agent, or Firm—Blodgett & Blodgett

[57] ABSTRACT

Apparatus and a method for detecting the presence of incidental bubbles in liquid flowing in a tube. The system monitors the amplitude of microwave radiation from the liquid and recognizes when that amplitude drops in a manner characteristics of the presence of a bubble.

5 Claims, 6 Drawing Sheets

MICROWAVE SYSTEM FOR DETECTING GASEOUS EMBOLI

BACKGROUND OF THE INVENTION

Background—Clinical Need

The hazard of air embolization related to either cardiotomy or pump oxygenator accident is well recognized by all cardiac surgeons. Air embolism can cause devastating injury in the distribution of both the coronary and cerebral circulations. In the experimental animal, air in quantities of 0.5 cc/kg injected into the left side of the heart can cause death from coronary embolization. When air is injected into the carotid artery of the dog, 0.25 ml/kg causes marked neurologic damage.

It is generally believed that the most frequent source of air embolization is air trapped in the left heart chambers related to cardiotomy, and research efforts are still being directed in this area, since this hazard is not yet completely solved. Neurologic sequelae after coronary artery operations without cardiotomy, although less common, continue to be seen occasionally and may be related to air or particulate emboli in the ascending aorta.

The hazard of air introduction during aortic cannulation, related to manual squeezing of the clamped air-containing cannula during its introduction has been pointed out by researchers. In this application a small device, such as the radiometric antenna, that could be clamped onto the cannula configuration might be useful in detecting small emboli.

Other applications of an air emboli detection device include angiographic examinations. These procedures have become routine in even small hospitals throughout the country. The introduction of air into the vascular system, especially during intracerebral examinations, is an occurrence which, expectedly, has great morbidity and mortality. The potential for inadvertent introduction of air is present each time an angiographic study is performed. The mechanism of damage due to air emboli is not well understood, but the devastating effect, especially in the cerebral and coronary circulations, is well known. The clinical problem which has precipitated an intracerebral angiographic examination may be mimicked by the introduction of air into the cerebral vessels. Therefore, the occurrence of air emboli may not even be suspected.

Currently, the only method to insure that no air is introduced into blood vessels during the angiographic examination is the adherence to meticulous angiographic technique. Visual detection of air bubbles in the system and their removal prior to injection of contrast agents is the only current method available. For obvious reasons no one has done a controlled study on humans to see what quantity of air introduced into carotid or vertebral arteries would be necessary to result in clinical signs. Even small amounts of air however would be expected to have the potential for clinical sequelae. Canine studies suggest that air emboli of 1 ml injected into a pulmonary vein result in death from coronary air embolism. Arterial air emboli of approximately 0.5 ml in humans are of sufficient size to cause fatal arrhythmias from focal coronary ischemia. One might reasonably expect the critical lethal air embolus volume in the cerebral circulation to be even less than 0.5 ml. As previously mentioned, it is difficult, if not impossible, to state with certainty the critical volume of air emboli which result in morbidity. Given that fatal air emboli of 0.5 ml or greater should routinely be detected visually by careful techniques, a system to detect air emboli would need to be sensitive to bubbles of 0.1 ml or smaller to routinely detect the smaller bubbles which have greater potential to be "missed" by careful techniques.

An effective air embolus detection device would have application to all pump oxygenator and contrast injection systems currently in use throughout the health care delivery system. In order for an air emboli detector to be of value clinically, it must be designed such that it does not prolong the existing procedure (for example, complications in angiography are directly related to the amount of time that the catheter is actually within the vascular system). Ideally, the device should be able to be used without necessitating additional steps in the usual manipulation of catheter, stopcock and pump. To be able to have the detecting device somehow integrated into an existing part of the system would be ideal, as would having the device be sterilizable and/or disposable. The detection device must be "in line" throughout the procedures.

Background—Survey of Other Technologies for Air-Bubble Detection

At the present time, there appears to exist only one commercially available "stand-alone" unit for air-bubble detection. This device, marketed by Sarns Inc., uses a light source and detector mechanism. It has been reported to have a limit of detecting air bubbles no smaller than one ml in volume ("Cardiopulmonary Bypass", CC Reed and TB Stafford, Texas Medical Press, 1985, pt. 485). The optical technique also has other limitations. It is not useful for detecting air bubbles in opaque tubing or detecting air bubbles not on the outer surface for opaque fluids (e.g., blood).

Recently bubble detection involving ultrasound techniques have been introduced. These devices, however, are normally not "stand-alone" (i.e., they must be integrated into the fluid delivery system). Literature, including research at the University of Arizona supported by NCI Grants CA33922 and CA46627, indicate the attenuation of ultrasound energy in plastics is very high. Generally, it is recommended not to use plastic-coated tranducers or probes in ultrasound fields. The plastic, having significant wall thickness, creates a large acoustic impedance mismatch coupled with high attenuation which will seriously degrade performance. A window must, therefore, be provided in the plastic or IV tubing, requiring interruption of the fluid path. Most recently, a "stand-alone" system employing an ultrasonic burst (radiated and detected) has been introduced. It claims to recognize 500 micron (2 microliter) bubbles.

Although other unexplored technologies may be able to be used for air bubble detection, the success of the radiometric technique in detecting air-bubbles *as small as 0.02 ml* (as explained below) does not warrant exploring these other technologies, particularly since the radiometric technique is efficacious and cost-effective.

Regarding the efficacy of microwave radiometry, the technique is a *passive* method detection. Other techniques such as ultrasound or active microwave methods, involving return loss measurements, require active signal sources. *Active microwave techniques* such as the monitoring of impedance changes would require the use of an *active transmitting source in addition to a receiver*

*module*. The radiometry method requires only a receiver module.

The use of radiometry would also simplify the FDA approval process of the device. This would be an advantage over active (signal transmission) methods since a device that transmits energy into a circulation path used for an in-vivo procedure would require an investigation into the effects of such a process on the fluid passing through the energy field.

Based on the preliminary results and the cost projections of the radiometric device, which is the subject of this invention, improvement on existing technology (e.g. the Sarns product) is possible by detecting air-bubbles:

1. Smaller than 1 ml
2. More quickly
3. Less expensively.

Regarding cost/performance issues, the present inventor has developed a small, low-cost microwave radiometer for use in other medical applications. In particular, as part of a recently completed SBIR Phase II contract sponsored by NIH (Contract #N44-CM-77821) a Radiometric Extravasation Detection system has been designed, developed and fabricated. The system was successfully *completed* and *demonstrated*. This radiometer is small enough to be hand-held. The Phase III follow-on program to NIH Contract #N44-CM-77821 has been established.

Background—Radiometric Detection Method

Utilization of the proposed microwave technique would constantly monitor the fluid lines for air emboli and would contain the capability of automatically shutting down the fluid flow if air were detected. Detection is accomplished with a sensitive microwave radiometer specifically designed to sense variations in microwave radiation by a passive noninvasive technique.

Radiometry is a measurement of the received radiation or electromagnetic energy considered as thermal radiation. From "black body" theory, any perfectly absorbing body emits radiation at all frequencies in accordance with Planck's radiation law. The distribution of radiation, shown diagrammatically in FIG. 3, is a function of both temperature and wavelength, or frequency. As the temperature of the black body increases, the intensity of the radiation at all frequencies also increases. From this fact infrared thermography, or infrared radiometry, would appear to be most effective. However, the depth of penetration, or emission, becomes a limiting factor. At infrared frequencies, this depth is so small that emission turns out to be merely dependent of the surface temperature of the black body. An appreciable amount of radiation exists at the microwave segment of the spectrum. The reduction in emissivity at the microwave frequencies is offset by the reduced transmission loss.

The principle of operation of the radiometric technique is fully described in the literature. The design of the radiometer is based on the technique of comparing the level of electromagnetic noise emitted by an unknown source to a reference or stable noise sourse. The technique and implementary devices were proposed by Dicke [R. H. Dicke, "The Measurement of Thermal Radiation at Microwave Frequencies", The Review of Scientific Instruments, Vol. 17, No. 7, July 1946].

Basically the radiometric detection process involves the measurement of the emissivity of the fluid/air mixture in the target zone within a waveguide. Any object above absolute zero will radiate electromagnetic energy to an extent governed by its radiant emittance. A body upon which electromagnetic radiation falls may transmit, reflect or absorb radiation. A body which absorbs all of the incident radiation or energy is known as a "black body". To remain in equilibrium, a perfect absorber is also a perfect emitter, or radiator, and from "black body" theory, any perfectly absorbing body emits radiation at all frequencies in accordance with Planck's radiation law. The distribution of radiation is a function of both the temperature and the wave length, or frequency. FIG. 3 shows a graphical representation of intensity of black body radiation as a function of temperature and frequency. A liquid (e.g., blood) is very emissive at electromagnetic frequencies compared to air. An air bubble has no microwave attenuation and therefore does not emit energy. Therefore, a bubble would have a substantial impact on the level of emission as the bubble passes by a detection aperture or target zone. To optimize the detection process, target zone would tend to be small. A reduction in waveguide size would, in effect, permit an air-bubble of a given size to occupy a larger relative portion of the aperture, thus increasing the detected signal difference between a liquid-filled line and a line with an air-bubble.

It is the microwave portion of the black body emission that this invention proposes detecting using a microwave radiometer. The fluid in the tubing can be considered the emitter, or microwave generator. Liquids have much higher absorptive characteristics than air and thus will transmit more electromagnetic energy toward an antenna. With an appropriate antenna design, the microwave signal emitted by the fluid would be received and processed through the microwave radiometer. Since air is lossless at microwave frequencies, it conversely will have negligible emission; therefore an air bubble in the liquid would appear as a significant reduction in emitted signal.

The 4.7 GHz radiometer has been demonstrated to detect subsurface thermal difference in several applications. One such application, is the detection of the occurrence of the extravastion of cool (room temperature) fluids from an infusion line. See U.S. Pat. No. 4,647,281. Using a waveguide antenna placed over the injection site, the radiometry system is able to distinguish between normal IV flow and an extravasation event for even very *slow flow rates* as 0.03 ml/sec ((100 ml/hr).

Another application amenable to microwave radiometry is the measurement of fluid temperature flowing through tubing. See U.S. Pat. No. 4,715,727. The present invention has successfully demonstrated that differences in fluid temperature can be measured with a microwave radiometer.

In summary, prior art gaseous emboli detecting systems have a number of faults. In some cases they are simply not cost-effective. In other cases, they are not sufficiently accurate or reliable for clinical use.

These and other difficulties experienced with the prior art devices have been obviated in a novel manner by the present invention.

It is therefore, an outstanding object of the invention to provide a reliable, accurate and cost-effective system for detecting gaseous emboli in liquid streams.

With these and other objects in view, as will be apparent to those skilled in the art, the invention resides in the combination of parts set forth in the specification and covered by the claims appended hereto.

SUMMARY OF THE INVENTION

Accidents involving the introduction of air emboli in the coronary or cerebral circulation paths through cardiotomy or pump oxygenator procedures can result in devastating injury. Proposed here is a non-invasive mechanism for quickly and accurately detecting the presence of air emboli in the infusion path. This would help reduce the risk associated with such procedures.

The goal of the proposed system is to adapt an existing microwave radiometry system with appropriate target antennas to "see" air emboli traveling through plastic or glass tubing used to deliver fluid/blood to a patient. This radiometric technique monitors the noise level emitted by fluid flowing through a transducer containing a microwave antenna. Since the noise level of the target is a function of its dielectric properties, this system will in effect monitor the fluid-to-air ratio of the media within the boresight of the antenna. Using this principle, transducers and associated circuitry can be developed to optimally detect the presence of even very small air emboli within infusion lines. The sensitivity and specificity of the system will be determined as a function of parameters such as tubing size, fluid type, fluid flow rate, fluid line pressure, fluid temperature and air bubble size.

The proposed microwave radiometry monitoring technique for detection of the presence of air emboli is a non-invasive, sterile and passive method with a fast response time. These characteristics will ultimately make conventional cardiopulmonary bypass procedure safer. Furthermore, using state-of-the-art hybrid and monolithic microwave circuit technology, a small low-cost system is achievable.

BRIEF DESCRIPTION OF THE DRAWINGS

The character of the invention, however, may be best understood by reference to one of its structural forms, as illustrated by the accompanying drawings in which.

DESCRIPTION OF THE PREFERRED EMBODIMENT

Technical Objectives

The purpose of this project is to develop a microwave radiometry system for use in non-invasive detection of the presence of air in extracorporeal circulation or infusion pathways used to administer blood or other fluids to patients. There are at least two urgent applications for such a system: (1) Detection of bubbles in the extracorporeal circulation circuit during cardiotomy or pump oxygenator procedures and (2) Detecting air emboli in contrast agents delivered during diagnostic imaging procedures. For the first application mentioned, the presence of foam is often a problem. Thus, a device that could detect very small bubbles (in the order of <0.1 ml in volume) would be of great benefit.

A program was established to determine the sensitivity and response time of radiometric detection of air bubbles. Preliminary test results show that, with the existing design, bubbles as small as 0.02 ml in volume can be detected. These results far exceed the reported limit of a one ml air bubble detection capability provided by a commercial unit that uses optical technology ("Cardiopulmonary Bypass", CC Reed and TB Stafford, Texas Medical Press, 1985, pg. 485.). Furthermore, modifications to the existing design can enhance performance to detect air bubbles even less than 0.02 ml in volume.

One obvious advantage of the microwave radiometry technique is that it is a *passive* technique, unlike optical, ultrasonic or other microwave techniques such as "return loss" monitoring. In addition, optical techniques are limited when the tubing is opaque or cloudy and when the bubble is in opaque fluids (e.g. blood) and is not on the outer surface of the tubing.

The *principal objectives* of this program were:
1) Optimize antennas to measure the microwave signal emitted by fluid flowing through plastic or glass tubing.
2) Optimize the impedance match for the interface between the antenna and a 4.7 GHz microwave radiometer.
3) Investigate the performance of the air detection technique at several radiometric frequencies.
4) Determine the sensitivity and specificity of the technique with regard to bubble size, tubing size, fluid type, fluid flow rate, fluid line pressure and fluid temperature.

Figure 1:
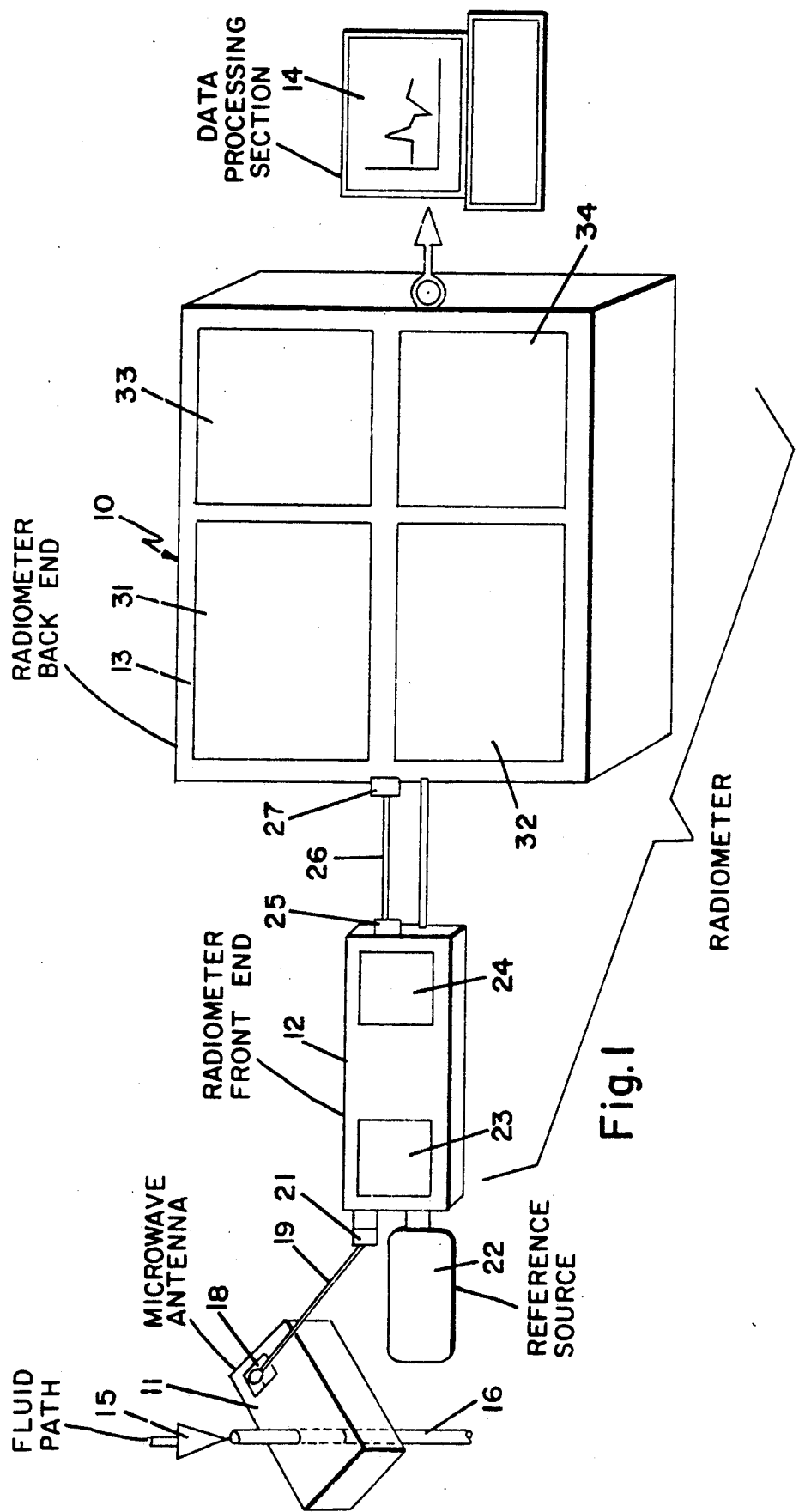
FIG. 1 is a diagrammatic representation of the system embodying the principles of the present invention.

The present radiometric air-emboli detection system represented in FIG. 1. This system employs a 4.7 GHz radiometer to measure electromagnetic energy emitted by the target within the boresight of the antenna.

Figure 10:
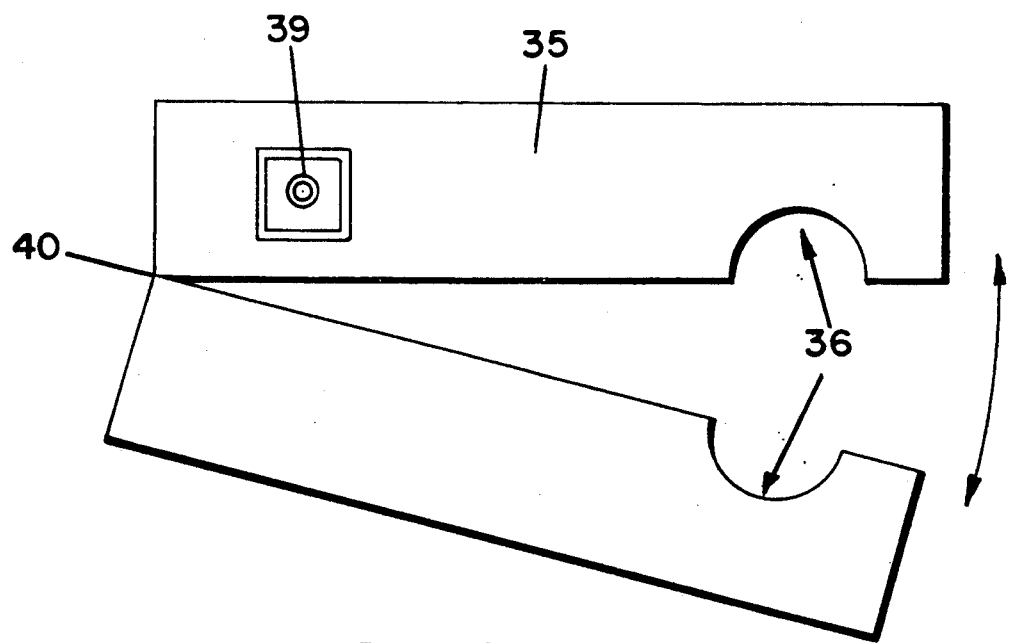
FIG. 10 is a diagrammatic top view of a waveguide section.

The emboli detection system shown in FIG. 1 and denominated generally by the FIG. 10, is shown to include a wave guide target antenna 11 which encloses the flow path of the fluid flowing in plastic tubing 16, a front-end electronics section 12, physically and electrically associated with the antenna 11, a back-end electronic section 13, electrically connected to front-end electronic section, and a data processing section 14, electrically connected to the back-end electronic section.

The fluid flowing path 15, which is the subject of the detection system of the present invention, is shown enclosed within plastic tubing 16. The signal which is representative of the microwave radiation from the target zone within the antenna (essentially a box filled with air or another dielectric) is fed to a connector 18 which is electrically connected by a microwave link 19 to a connector 21 on the front-end electronic section 12. Associated with the front-end electronic section is a reference source 22 which might be an antenna or a 50 ohm load.

Within the front-end electronic section 12 is a diode switch 23 and a low-noise amplifier 24. An exit connector 25 on the front-end electronic section 12 is connected to a microwave link 26 which is connected to an input connector 27 on the back-end electronic section. In a typical set up, a power cable would feed power front the back-end electronic section to the front-end electronic section to power the components of the front-end section. Typically, the front-end section 12 of the system would be very compact and provide low noise detection and would be located in close proximity (actually integrated with or as close as possible) to the antenna 11. The front end would be connected to the antenna by a microwave shielded cable. The back-end section could be integrated with a remote from the front-end.

The typical back-end electronic section 13 includes a lock-in amplifier section 31 which includes a base line for setting offset, a sensitivity element for adjusting gain, a resolution element as an integrator and a synchronization element which generates a square wave and sends it to the front-end section. A microwave section 32 includes filters, amplifiers and a detector. An output module 33 controls the voltage out and any displays associated with this part of the device. A power supply 34 for the unit includes either an AC to DC converter or batteries.

A signal transfer link connects the back-end electronic section 13 to the analogue input section of a data processing section 14, which is generally formed of a personal computer hardware setup and software suitable for acquiring and processing the signal into a useful presentation for the user.

Figure 2:
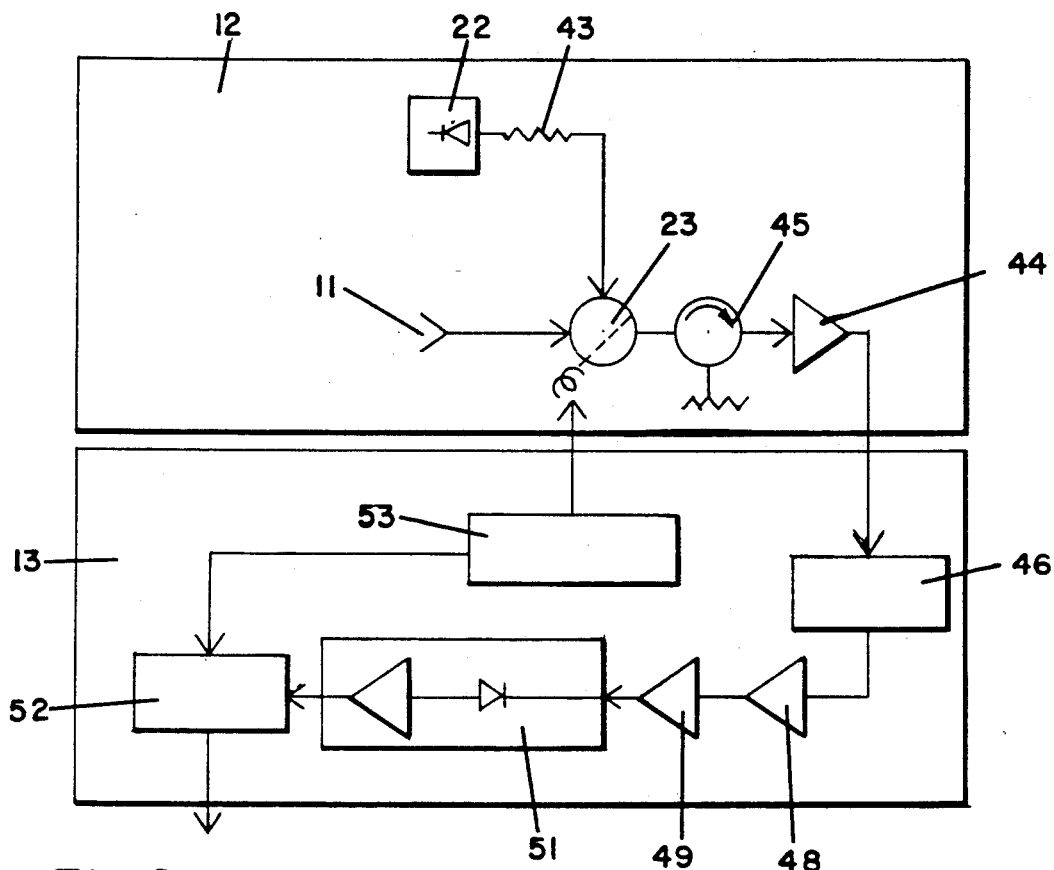
FIG. 2 is a diagrammatic representation of a radiometer which could be employed as a part of the present invention.
Figure 3:
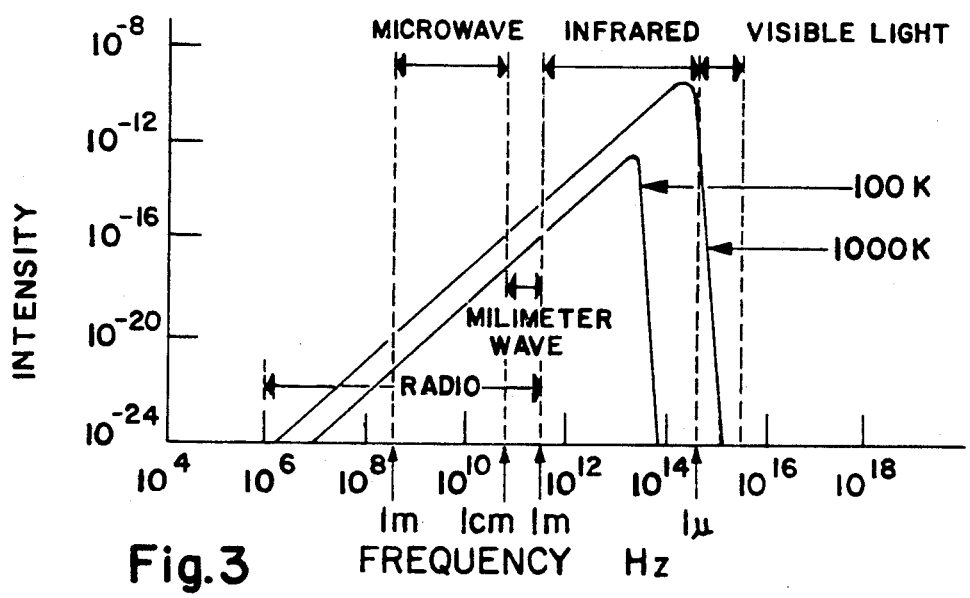
FIG. 3 is a graphical representation of the intensity of black body radiation.

Referring to FIG. 2 our diagrammatic representations of the various electronic elements within the front-end electronic 12 section and the back-end electronic section. The stable reference noise diode 22 feeds into a fixed attenuator 43, which, in turn, feeds into Dicke switch 23. The target antenna 11 is connected to the single pole double throw Dicke switch 23. The output of the Dicke switch is fed to a ferrite isolator 45 and then the signal is transferred to a low-noise amplifier 44 connected in turn to a filter 46 in the back-end electronic section 13. The output of filter 46 is fed to a radio frequency amplifier 48 and then another radio frequency amplifier 49. Next, the signal is fed through a square law detector and video amplifier section 51 and then on to a lock-in amplifier 52. Then the signal is passed out of the back-end electronic section into the data processing section. A one hundred Hz square wave driver 53 provides a synchronizing signal to the Dicke switch 23 and to the lock-in amplifier 52.

Technological Innovation

A reliable method of detecting the presence of air emboli in an infusion line is truly practical only if the method does not interfere with the infusion process itself. The microwave radiometric method described is *passive*, has a *rapid response* and maintains a *sterile* environment within the infusion pathway. *Passive* monitoring of the infusion line is inherent with the microwave radiometry since this technique employs an antenna to *receive* electromagnetic energy emitted by the target. A *rapid response* to changes in the constituency of the target is possible because the change in electromagnetic energy emitted by fluid as compared to air is quite significant. A *sterile* environment can be maintained during monitoring of the infusion line because at microwave frequencies, plastic and glass are transparent to the electromagnetic energy. Thus, the antenna can be placed on the *outside* of the tubing to measure the energy level of the fluid/air mixture inside the tubing.

The schematic for an existing 4.7 GHz radiometer, is shown in FIG. 2. The circuitry has been implemented using microwave hybrid circuit techniques and packaged in the configuration shown in FIG. 1.

The key innovation proposed here is to configure a waveguide antenna and use the radiometry system to measure (monitor) the electromagnetic energy emitted by fluid traveling through a plastic or glass infusion line. Air emboli would be detected by a significant deviation in the baseline signal level output by the radiometer for a fluid filled infusion line. The technical feasibility of this technique for commercial applications is achieved by optimizing the existing monitoring system so that it minimally impacts the configuration of existing infusion lines. The proposed system would provide an antenna of reduced size and weight that can "snap-on" to an existing and unmodified syringe or infusion line and still provide enough signal sensitivity.

EXPERIMENTAL DESIGN AND METHODS

Configuring the Radiometry System for use in Emboli Detection

The present inventor has designed and developed a 4.7 GHz microwave radiometer depicted in the block diagram and schematic of FIGS. 1 and 2. Basically it consists of an antenna designed to be impedance matched to the column of flowing fluid. The antenna is connected to a front end section of the radiometer which contains a diode switch and a low noise amplifier. The switch is used to alternate the signal going to the amplifier between the antenna and a reference antenna or stable noise diode. The low noise amplifier is a FET device constructed on microstrip. The amplified radio frequency (RF) signal is finally processed in the back section which contains a bandpass filter, additional RF amplification stages, a detector and lock-in amplifier. A remote power supply is used to generate the required dc supply voltages.

The radiometer is of a Dicke type design, which greatly reduces the effects of short-term gain fluctuations. The receiver input is switched at a constant rate between the antenna and a constant temperature reference load. The switched, or modulated, RF signal is therefore inserted at a point prior to RF amplification and as close to the antenna as possible. The signal is then amplified and coherently detected. The final output is proportional to the difference in microwave emission between the signal received by the antenna and the reference load.

Since long-term gain variation should not be a problem, the inventor anticipates utilizing a built-in termination as the reference load. Other alternatives for the reference load would be an additional reference antenna, a noise source, or a thermal load.

Configuration of the Data Collection System

Figure 5:
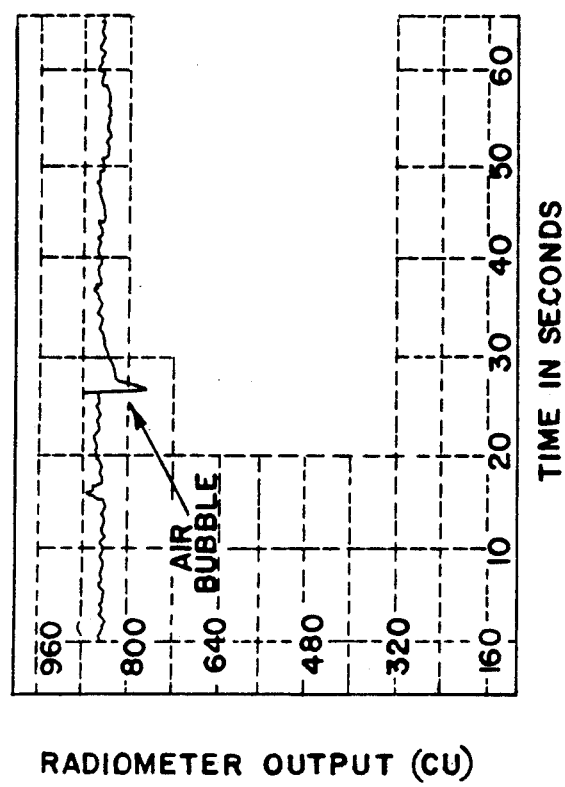
FIG. 5 is a graphical representation of the output signal responding to a relatively small bubble.
Figure 4:
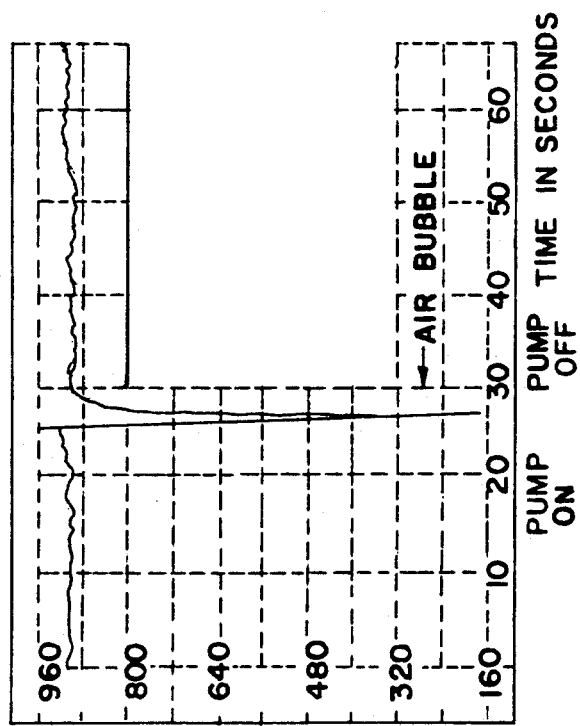
FIG. 4 is a graphical representation of the output signal responding to a relatively large bubble.

A low-cost microcomputer system based on the IBM-PC computer can be used for characterization studies. A laboratory software package (ASYST ™ from Macmillan Software Company, New York) has been used extensively by the inventor to collect radiometric data in a controlled manner. This laboratory software package provides user selectable menus for controlling a commercially available analog-to-digital interface plugged into the IBM PC bus. Using this procedure, records of data are displayed graphically, in real-time, on a monitor and stored on disk for later analysis. Examples of the graphic display of data are shown in FIGS. 4 and 5. The data in both FIG. 4 and FIG. 5 were acquired with Renogralin-60-brand opaque contrast fluid flowing in the tube at 1 ml/sec. The converter unit (cu) equaled 0.00488 volts. FIG. 4 shows a response to a 0.2 ml air bubble. The response (baseline to nadir) was 726 cu with a slope of 1820 cu per second. FIG. 5 shows a response to a 0.02 ml air bubble. The response (baseline to nadir) was 65 cu with a slope of 325 cu per second. The resolution of the data is determined by the range and speed of the analog-to-digital converter. Currently, a 10-bit converter is being used with a sampling rate of 1 sample per 100 milliseconds. Better resolution is required to quantify the response of the system to air bubble detection particularly at flow rates of 1 ml/sec or greater. The analog-to-digital conversion software can be modified to implement an increase of 4 to 5 times the present sampling rate.

In addition, a simple detection algorithm can be implemented, in software, to detect an excursion of the radiometric output signal below a specified threshold. Upon detection of an excursion below the threshold, the digital-to-analog interface circuitry on the IBM PC will be used to trigger a relay circuit that can, in turn, shut off a pump. Using this method, the position of the bubble when the pump stops can be visually observed. This procedure is a quantitative method for determining the distance of bubble travel after detection.

Determining Optimum Matching Interface between Antenna and Radiometer

Since this invention involves measuring the difference in microwave signal levels emitted by fluid and by air, it is evident one of the most important components will be the antenna, or transducer, used to couple the RF energy, emitted by the target, to the radiometer. The impedance match between the column of fluid and the receiver must be optimized so that maximum transfer of emission from the microwave generator (fluid, air) occurs.

The inventor proposes using a waveguide antenna as the means of receiving the $TE_{10}$ propagation mode. The plastic tubing will pass through the waveguide and, as it does, the microwave emissions 37 will disperse in the waveguide and be coupled to the radiometer (See FIG. 7). An advantage afforded by waveguide is that a shielded structure is provided that eliminates possible interference from other sources of noise such as fluorescent lamps. Preliminary experiments, performed thus far at 4.7 GHz using a waveguide antenna with a cross-section of 4.75×2.21 cm, have shown that air emboli as small as 0.02 ml in 0.125" I.V. tubing can be detected (See FIG. 5 and Table 1).

TABLE 1

SUMMARY OF AIR EMBOLI DATA
(The nadir for each of these trials occurs approximately 0.1 to 0.3 secs after the initial downward excursion.)

| PUMP SPEED ml/sec | BUBBLE VOLUME ml | BASELINE AVERAGE cu* | BASELINE Std Dev cu* | BUBBLE NADIR cu* | MAX RESPONSE baseline-nadir cu* |
|---|---|---|---|---|---|
| 10 | 1 | 822 | 10 | 619 | 203 |
| 10 | 0.5 | 810 | 6 | 705 | 105 |
| 10 | 0.2 | 822 | 6 | 799 | 23 |
| 5 | 0.5 | 802 | 7 | 529 | 273 |
| 5 | 0.2 | 801 | 6 | 698 | 103 |
| 5 | 0.1 | 804 | 5 | 778 | 26 |
| 1 | 0.5 | 900 | 6 | <0 | >900 |
| 1 | 0.2 | 904 | 5 | 178 | 726 |
| 1 | 0.1 | 880 | 8 | 543 | 337 |
| 1 | 0.05 | 847 | 7 | 628 | 219 |
| 1 | 0.02 | 843 | 6 | 776 | 67 |
| 0.5 | 0.5 | 867 | 7 | <0 | >867 |
| 0.5 | 0.2 | 900 | 4 | <0 | >900 |
| 0.5 | 0.1 | 886 | 5 | 114 | 772 |
| 0.5 | 0.05 | 886 | 9 | 539 | 347 |
| 0.5 | 0.02 | 842 | 7 | 635 | 207 |

*NOTE: cu = analog-to-digital converter units, where 1 cu = 0.00488 volts

Figure 6:
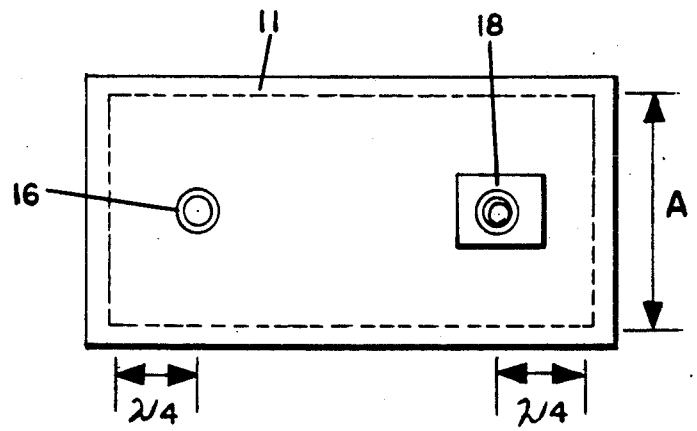
FIG. 6 is a diagrammatic top plan view of a waveguide antenna section of the present invention.
Figure 7:
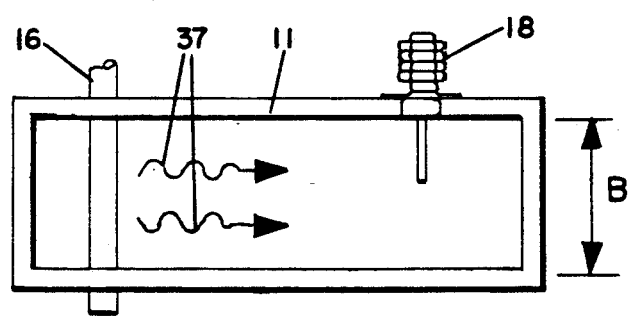
FIG. 7 is a diagrammatic side elevation view of a waveguide antenna section of the present invention.

The coaxial connector shown in FIGS. 6 and 7 contains an E Field probe 38 that protrudes into the waveguide. This probe or launch is located at the point of maximum E Field which corresponds to a point λ/4 from the short circuit. This is the point of maximum coupling. Similarly, locating the fluid filled tubing an equivalent distance, λ/4, from a short circuit will optimize propagation along the waveguide toward the probe.

Reducing Size of Existing Antenna: Dielectric Loading

The magnitude of the signal detected by the antenna is proportional to the ratio of fluid to air inside the tubing traversing the antenna. For a given fluid type, the maximum signal will be achieved when there is 100% fluid and 0% air. Likewise, the minimum signal is achieved when there is 0% fluid and 100% air. Thus an indication of air presence is given when the magnitude of the signal detected is at a level lower than that with 100% fluid.

Figure 8:
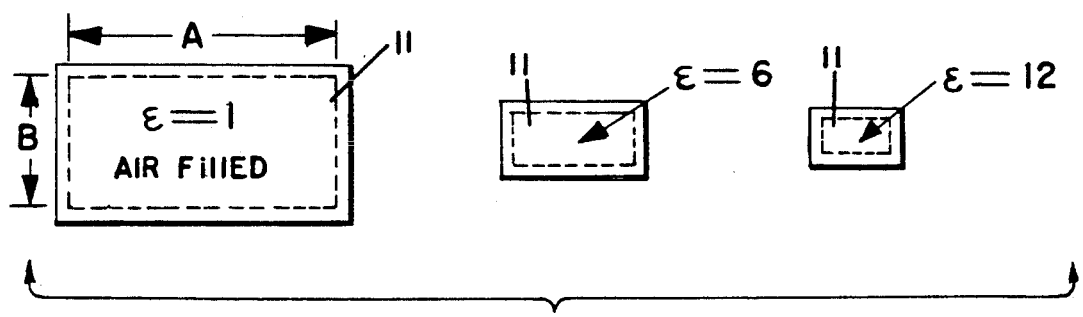
FIG. 8 is a diagrammatic view of various waveguide geometries.
Figure 9:
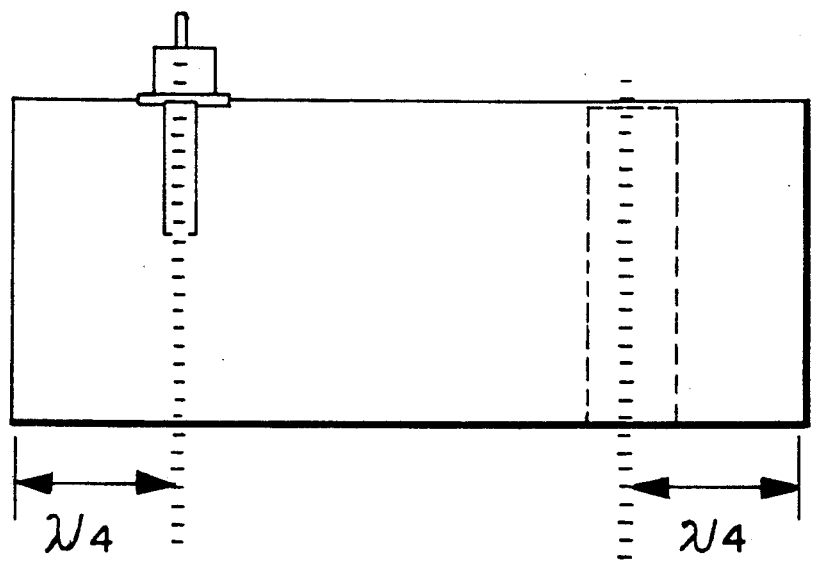
FIG. 9 is a diagrammatic side elevation view of a waveguide section.

A smaller waveguide profile can be achieved by dielectrically loading the waveguide. The "A" and "B" dimensions indicated in FIGS. 6 and 7 can be reduced by the square root of the dielectric constant of the dielectric filler. In the case of the 4.75×2.21 cm waveguide, use of a dielectric filler with E=6 would result in new waveguide dimensions of 1.94×0.90 cm (See FIG. 8). A given fluid filled tubing will now occupy a larger portion of the total waveguide cross-section increasing the transmission loss. This, in turn, will result in increased emissivity. The smaller waveguide configuration should therefore allow detection of smaller air bubbles.

An alternate means of size reduction can be accomplished with reduced height waveguide. In this case, the "B" dimension is decreased. This decrease effects the waveguide impedance but not the operational frequency of the $TE_{10}$ mode.

Determining Optimum Frequency of Operation

The selection of microwave frequency for detection and the antenna design will be important for optimum performance. Tests to date have indicated that air bubbles can be detected if the bubble occupies a significant portion of the volume of the tubing within the waveguide. Since waveguide size decreases with increasing frequency and radiated intensity in the microwave region increases with increasing frequency, it would seem reasonable to use a high frequency radiometer. However, if the frequency is too high, the problem of penetration depth occurs as in the case of infrared thermography. At the extreme, mainly surface temperature would be detected.

The size of the air emboli with respect to the waveguide size is the important factor. One should compare a system operating at 4.7 GHz with dielectric-filled waveguide to a system operating at some higher frequency with an air-filled waveguide.

Consideration of a higher microwave frequency than 4.7 GHz should also be considered. The advantage would be that a smaller antenna cross-section could be achieved with air-filled waveguide. The air-filled waveguide gives optimum performance since introduction of a dielectric filler results in somewhat higher loss. In addition, since emissivity increases with increasing frequency, the contrast between the liquid and the air (bubble) is greater at millimeter frequencies. The inventor prefers a frequency near 22 GHz as the components are readily available for an appropriate radiometer. Such a radiometer could be built using discrete components previously developed for low noise receivers for both military (MILSTAR) and commercial communications systems.

As an example: If operation were selected in the 20-24 GHz frequency range and air-filled waveguide was desired, the inventor would recommend WR-42 waveguide. This has a cross-section of $1.07 \times 0.43$ cm. If the radiometer had the same sensitivity as a system at 4.7 GHz, the bubble size of 0.02 ml detected at 4.7 GHz could be reduced to 0.002 ml.

To evaluate performance over the frequency range of 20-24 GHz will require the following components in the WR-42 waveguide (1) Ferrite Latching Switch, (2) Ferrite Isolator, (3) Low Noise Amplifier and (4) Dectector. Circuitry following the detector would be identical to the described 4.7 GHz radiometer.

Configuring Antenna into a Package That Can Easily Be Clamped onto an Existing Infusion Line The development of a low cost, portable, and user-friendly monitoring device is the objective of this invention. A miniature radiometer operating at 4.7 GHz has already been developed. The transducer, or waveguide antenna, must be designed to be compatible with various I.V. tubing diameters. For the antenna, the inventor prefers the clam-shell configuration 35 shown in FIG. 10. In this case, the coaxial probe 39 is located off center and the waveguide is hinged, at hinge 40, at one end so that it can be opened to receive the tubing. Since tubing size may vary, an insertable low loss tubing holder 36 could be provided to firmly hold the tubing in place.

Splitting the waveguide along the broad wall or E plane will minimize leakage or coupling and, therefore, minimize possible interference from other noise sources such as fluorescent lamps.

Configuring the Experimental Test Fixture

Figure 11:
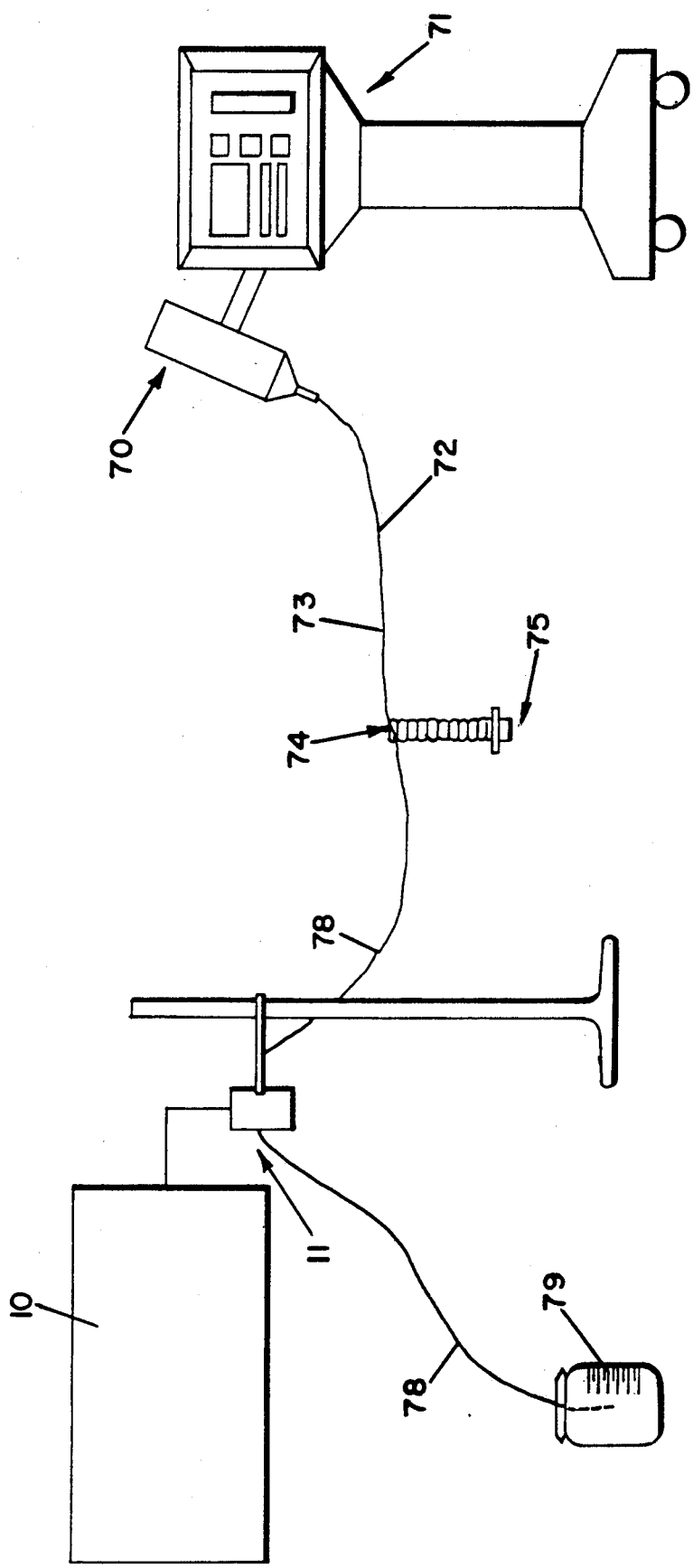
FIG. 11 is a diagrammatic view of a test system for testing the present invention.

The test fixture, presented schematically in FIG. 11, was used to generate the preliminary data shown in Table 1. Starting from the right of the diagram, a Medrad Mark V Radiographic Contrast Injector 71 drives a fluid injection syringe 70 which is connected to two pieces of flexible plastic tubing with Luer-Lock fittings. The first length of tubing 72 is 29 cm long with an OD of 0.55 cm and volume of 1.5 ml. The second length of tubing 73 is 28 cm long with an OD of 0.52 cm and volume of 1.5 ml. Next a Y-connector 74 is fitted to a 1 ml tuberculin syringe 75 for the injection of air emboli. Finally, a 138 cm length of plastic tubing 78, (OD of 0.38 cm, volume of 6.8 ml) is passed through the microwave antenna 11, which is connected to the radiometer 10. The end of the tubing 78 is open and allowed to flow into a beaker 79.

The test fixture will be configured exactly as it would be used clinically. The tubing connected to the Medrad injector 70 will be run to a Y-connector 74 and then to various sizes of catheters. To achieve greater accuracy and reproducibility in the introduction of air emboli, especially at small embolus volumes, Eppendorf pipets may be used at the Y-connector in place of tuberculin syringes. Also, as a back-up measure, volumetric calibration marks will be place on each French catheter to double-check the volumetric displacement of each embolus. The temperature of the effluent contrast agent will be monitored using an Omega thermocouple temperature system which is routinely calibrated in a water bath whose temperature is monitored using a NBS-traceable mercury-in-glass thermometer.

The range and rationale for that range on each test parameter are discussed more thoroughly below. The practical limitation on flow rate due to fluid viscosity and tubing diameter is represented in Poisseuille's Law which states:

$$RF = \frac{\pi r^4 (P_1 - P_2)}{8Ln}$$

where: RF=flow rate, r=internal radius of tubing, P=pressure, n=viscosity, L=tubing length.

Characterization: Radiometric System Parameters

Characterization of antennas with different apertures and dielectric loading involves using the test fixture to measure the response of the system to the detection of air emboli traveling through a fluid-filled infusion line. Using a microwave radiometer operating at a given frequency, various antennas can be compared for their ability to detect air emboli under a constant set of experimental conditions. When comparing antenna A with antenna B, the same tubing sizes, flow rate, line pressures, fluid temperatures and air embolus volumes should be used. System response will be characterized by response rate (initial slope of voltage excursion caused by the air embolus) and total response or signal excursion, which must be reasonably large so that differences in signal excursion attributable to antenna A versus antenna B are discernable. Reproducibility should be assessed by replicated runs of the same sets of experimental conditions.

Characterization: Target System Parameters

Conditions simulating those occurring in clinical applications are addressed by collecting data for various target configurations. The range and rationales for each of the test system parameters are as follows:

1. Tubing sizes. Tubing sizes used in cardiopulmonary procedures (i.e., tubing sizes=⅛, ¼ diameter) and by angiography procedures (i.e., tubing sizes=4,5,6 and 7 French) will be used.

2. Fluid types. To simulate cardiopulmonary applications, saline and blood will be used. To simulate diagnostic imaging applications, both an ionic and nonionic contrast agent will be used.

3. Fluid flow rates. Four flow rates, covering the range of rates used inc cardiopulmonary and angiography procedures and, will be used. They are 1, 5, 10 and 30 ml/sec.

4. Fluid line pressures. The linear rise function of the pump will be used at three settings: none (0), 0.4 and 0.8 secs.

5. Fluid temperatures. Two real-life conditions will be simulated. The first condition involves no temperature manipulation (our laboratory room temperature is reasonably well-regulated between 22°–23° C.). The second condition is where the fluid is stored in a "hot-box" and then used in the injector with the heat cuff prior to use. In the latter case, an Omega thermocouple thermometer will be used to monitor temperature of the fluid as it exits the microwave antenna.

6. Air bubble sizes. Four sizes will routinely be evaluated, ranging from the easily visible but lethal 0.5 ml and down to 0.1, 0.05 and 0.02 ml. In certain cases, even smaller volumes of 0.01 and 0.005 ml will be used. These would represent the very small bubbles that frequently occur within the connectors of the injection system and which may not be seen easily even on careful visual inspection.

A minimum of three replicate runs of each set of variables would allow an estimate of the reproducibility of the system. Using these procedures, the minimum resolvable air emboli that can be detected for system and target configurations can be determined as well as system sensitivity and response rate.

Analyze Results

When an air embolus passes through the microwave antenna, there results a drop in output voltage in the radiometer system compared with previous baseline values when bubble-free fluid passes through antenna. (see FIGS. 4 and 5.) Two measures can be used to compare system performance. The first is the total response or signal excursion, which is the nadir output voltage subtracted from the baseline output voltage. Our preliminary results have shown this signal excursion to be directly proportional to the volume of the embolus and inversely proportional to pump speed. The second measure of system performance, and most probably the more important one in terms of utility for alarm purposes, is the initial slope of the downward voltage excursion. It is noteworthy that the downward voltage (beginning of pulse, left side) has a steeper slope than the return (end of pulse, right side) to baseline when the bubble has passed through the detector. Underlying reasons for this are being explored, but are not completely understood.

Test Results

The results collected thus far have established the effectiveness of the invention. FIG. 4 shows the radiometric output of the existing system, configured as in FIG. 1, when an air bubble of 0.2 ml travels through PVC tubing (0.125" inside diameter) carrying Renografin-60 at a flow rate of 1 ml/sec. In this figure, we see that the response of the radiometer output is rapid, showing a change of 726 analog-to-digital converter units (cu) in approximately 0.3 secs. The excursion due to the air bubble is well above the baseline noise level of approximately 5 cu. The lower limits of air bubble detection for the existing mechanism at the 1 ml/sec flow rate occur when the air bubble volume approaches 0.02 ml. FIG. 5 shows the system response when an air bubble of 0.02 ml travels through the tubing at a 1 ml/sec rate. This detection capability would satisfy the projected clinical requirement of detecting air bubbles of 0.1 ml in volume. In discussions above, we specified how the air bubble detection mechanism can be optimized to yield large radiometer output excursions when even very small bubbles ($\leq 0.02$ ml) pass through the system at high flow rates ($>1$ ml/sec).

A summary of preliminary data on air emboli is provided in Table 1. A range of pump speeds from 0.5 to 10 ml/sec and a range of air bubble volumes from 0.02 to 1.0 ml have been evaluated. With a constant pump speed, for example 1 ml/sec, decreasing the bubble size decreases the response. Also, keeping the bubble size constant, for example 0.2 ml, the response increases as pump speed decreases. These data represent single determinations at each of the specified parameters. Duplicate determinations showing excellent reproducibility have been made.

The sensitivity and response rate of the system to the detection of air emboli should be measured as a function of the following *system parameters*: antenna aperture, antenna dielectric loading, and radiometric frequency of operation. Data for each system configuration should be collected for the following *target parameters*: tubing size, fluid types, fluid flow rates, fluid line pressure, fluid temperature, and air bubble size.

Results form the initial study could provide enough evidence and data to determine the optimum design of the antenna itself and of the radiometer's operating frequency. The future program will continue this development to prepare for the commercial introduction of this device as follows:

Develop a series of antennas that could quickly be attached to different sizes of infusion lines or syringes using lightweight materials selected for ease of manufacturing.

Incorporate any changes to the system's frequency of operation in the radiometry circuitry.

Develop microprocessor-based circuitry to implement the detection algorithm, alarm mechanism and user interface.

Verify, using anesthetized large animals (dogs), that the air embolus detector detects experimental emboli under actual cardiotomy or pump oxygenator procedures. Likewise, verification will be made for the type of arterial or intravenous injections used for delivery of contrast agents during diagnostic imaging procedures.

Development of a mechanism to shut down or redirect the fluid can prevent the emboli from entering the patient.

It is obvious that minor changes may be made in the form and construction of the invention without departing from the material spirit thereof. It is not, however, desired to confine the invention to the exact form herein shown and described, but it is desired to include all such as properly come within the scope claimed.

The invention having been thus described, what is claimed as new and desired to secure by Letters Patent is:

1. A system for detecting the passage of gaseous emboli through a portion of conduit having liquid contents, comprising:

(a) a microwave radiometer which detects energy in the microwave spectrum, (b) a microwave waveguide which directs emitted microwave energy from the contents of the portion of the conduit to the radiometer, (c) a signal conversion section which converts the energy at the radiometer into an output signal related to the amplitude of microwave radiation from the contents of the portion of the conduit, (d) a source of a controlled reference signal, (e) means of comparing said output signal with said controlled reference signal, and (f) means of recognizing a change in the results of said comparison indicative of entry of a gaseous embolus into said portion of the conduit.

2. A system as recited in claim 1, wherein the liquid is a biologic fluid.

3. A system as recited in claim 1, wherein the liquid is blood.

4. A system as recited in claim 1, wherein the liquid is a biologic imaging fluid.

5. A method for detecting the passage of gaseous emboli through a portion of conduit having liquid contents, comprising the steps of:

(a) positioning a microwave radiometer which detects energy in the microwave spectrum, (b) positioning the portion of the conduit in a microwave waveguide which directs microwave energy from the contents of the portion of the conduit to the radiometer, (c) employing a signal conversion section which converts the energy at the radiometer into an output signal related to the amplitude of microwave radiation from the contents of the portion of the conduit, (d) producing a controlled reference signal, (e) comparing said output signal with said controlled reference signal, and (f) recognizing a change in the results of said comparison indicative of entry of a gaseous embolus into said portion of the conduit.

* * * * *